Oct. 13, 1953 H. A. M. VERSCHUREN Plant Pat. 1,223
ROSE PLANT
Filed Oct. 6, 1952
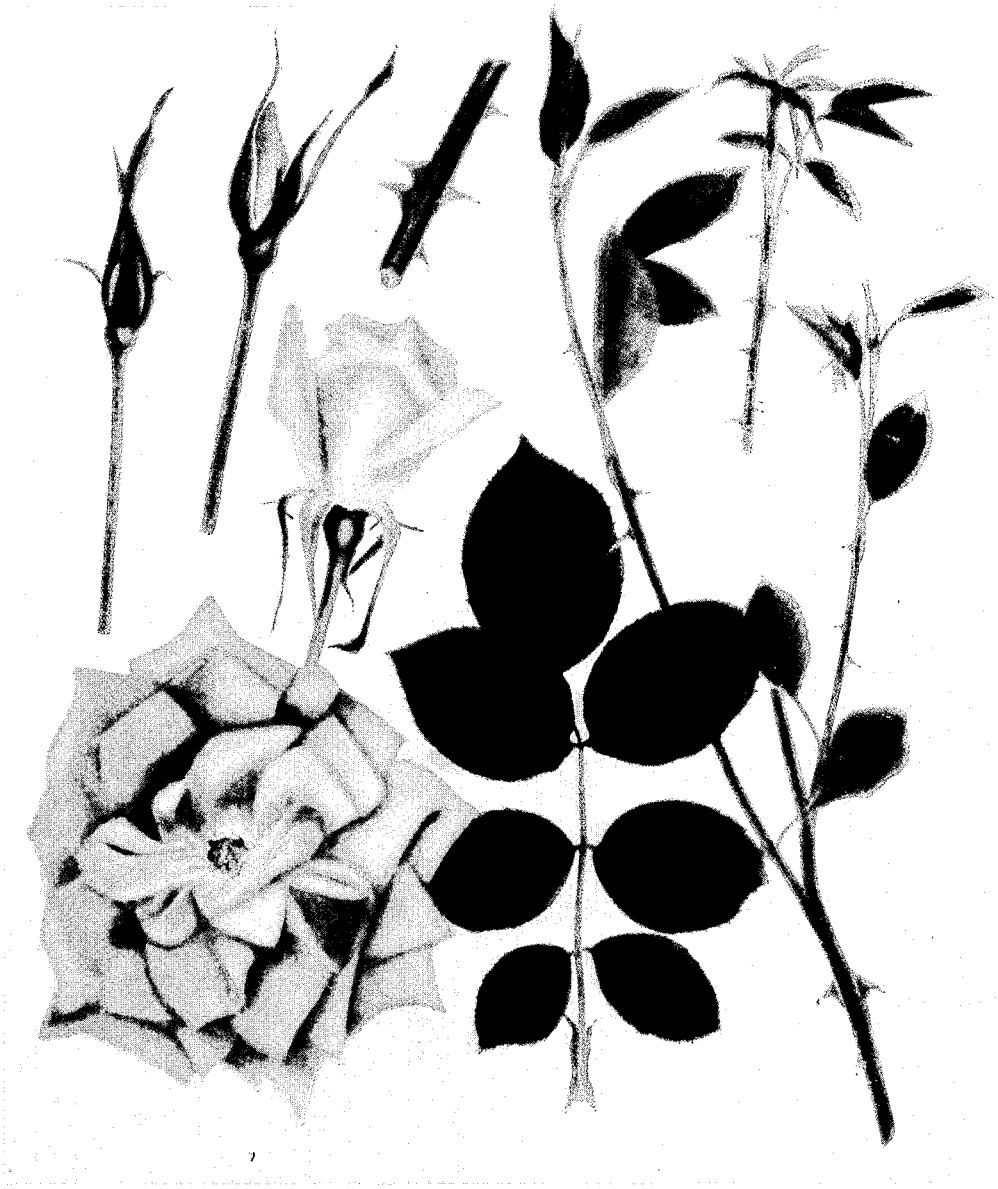
Inventor.
H. A. M. Verschuren
By: Robb & Robb
Attorneys.

Patented Oct. 13, 1953

Plant Pat. 1,223

UNITED STATES PATENT OFFICE 1,223

ROSE PLANT

Hendrikus Antonie Maria Verschuren, Haps, Netherlands, assignor to Jackson & Perkins Company, Newark, N. Y., a corporation of New York Application October 6, 1952, Serial No. 313,379

1 Claim. (Cl. 47—61)

The present invention relates to a new and distinct variety of rose plant of the hybrid tea class, originated by me by crossing the variety "Katherine Pechtold" (unpatented) with the variety "Crimson Glory" (Plant Patent #105).

The primary objectives in making this cross were to produce a flame-colored rose for greenhouse use with high productivity of flowers, and to increase the size and accentuate the color of the flowers of the variety "Katherine Pechtold."

These objectives were fully attained, as evidenced by the following characteristics which distinguish my new variety from the parents, as well as from all other varieties known to me:

(1) The bright Spectrum Red color of the flowers, lightly overcast with Scarlet Red and with a suffusion of Lemon Chrome at the base of the petals;

(2) The quick repetition of growth, the top eyes under the flowers breaking into long shoots even before the flowers are in full bloom; and (3) The long stems of the flowers, which give my new variety particular value for cut flowers.

Asexual reproduction of the new variety by budding at Newark, New York, and at Pleasanton, California, U. S. A., shows that the foregoing distinguishing characteristics come true to form and are established and transmitted through succeeding propagations.

The accompanying drawing shows specimens of the flowers of my new variety in various stages of development from a young bud to a fully open flower, and also shows specimens of the stems and foliage in various stages of development.

The following is a detailed description of the new variety, with color terminology in accordance with Ridgway's Color Standards and Nomenclature:

Parentage: Seedling.
- *Seed parent.*—"Katherine Pechtold."
- *Pollen parent.*—"Crimson Glory."

Classification:
- *Botanic.*—Hybrid tea.
- *Commercial.*—Hybrid tea.

*Flower*

(Observations made in the greenhouse at Newark, New York, U. S. A., in the early part of the month of June at about mid-afternoon.)

Blooming habit: Recurrent—continuous.

Bud:
- *Size.*—Large.
- *Form.*—Long and pointed: is not affected by wet or hot weather.
- *Color.*—When sepals first divide—Carmine, Plate 1. When petals begin to unfurl—Scarlet Red, Plate 1. When half blown: inside of petals—Scarlet Red, Plate 1, lightly overcast with Rose Red, Plate 12; reverse of petals—Rose Red, Plate 12, lightly overcast with Spectrum Red, Plate 1, with a suffusion of Lemon Chrome, Plate 4, in the lower half of the petal.
- *Sepals.*—Slightly branched; "hood" over bud. Curl back when petals begin to unfurl. Color: inside—Kildare Green, Plate 31; Outside—Grass Green, Plate 6.
- *Calyx.*—Shape—apple. Size—small. Aspect—smooth. Odor when rubbed—none. Color—Spinach Green, Plate 5.
- *Peduncle.*—Length—medium. Aspect—smooth. Strength—stiff; slender. Color—Biscay Green, Plate 17.
- *Opening.*—Opens up well; is not affected by adverse weather conditions.

Bloom:
- *Size.*—Large. Average size when fully expanded—4½ inches to 5 inches.
- *Borne.*—Singly.
- *Stems.*—Long; strong.
- *Form.*—When first open—high center. Permanence—flattens, with ends of some petals partially curling back.
- *Petalage.*—Double (full but open center). Number of petals under normal conditions—20 to 25.
- *Color.*—Center of flower—Spectrum Red, Plate 1. Outer petals—Spectrum Red, Plate 1, lightly overcast with Rose Red, Plate 1. Base of petals (aiglet)—Lemon Chrome, Plate 4. Inside of petals—Spectrum Red, Plate 1, lightly overcast with Scarlet Red, Plate 1. Reverse of petals—Rose Doree, Plate 1, lightly overcast with Begonia Rose, Plate 1, with a suffusion of Lemon Chrome, Plate 4, in the lower half of the petal. General tonality from a distance—Spectrum Red, Plate 1, lightly overcast with Scarlet Red, Plate 1.
- *Discoloration.*—General tonality at end of first day—Spectrum Red, Plate 1. Second day—Spectrum Red, Plate 1, overcast with Scarlet Red, Plate 1. Third day—Spectrum Red, Plate 1, lightly overcast with Scarlet Red, Plate 1.

Petals:
- *Texture.*—Leathery; is not affected by wet or hot weather.
- *Appearance.*—Inside—velvety; outside—satiny.

*Form.*—Oval.
*Arrangement.*—Imbricated (regularly arranged shingle-like).
*Petaloids in center*—Few; small.
*Persistence.*—Drop off cleanly.
*Fragrance.*—Moderate. Nature—Tea (average Hybrid Tea scent).
*Lasting quality.*—On the plant—long. As cut flower—very long.

*Genital organs*

Stamens, anthers: Medium size; many. Arrangement—regular around styles. Color—Capucine Orange, Plate 3.
Stamens, filaments (threads):
*Length.*—Long.
*Color.*—Bittersweet Orange, Plate 2.
Pollen: Color—Capucine Buff, Plate 3.
Styles: Columnar; uneven length; medium length; thin.
Stigmas: Color—Eugenia Red, Plate 13.
Ovaries: All enclosed in calyx.
Seeds: None.

*Plant*

Form: Bush.
Growth: Vigorous; upright.
Foliage: 5 to 7 leaflets.
*Size.*—Medium.
*Quantity.*—Normal abundance.
*Color.*—New foliage: upper side—Oil Green, Plate 5, lightly overcast with Garnet Brown, Plate 1; under side—Citrine, Plate 4, lightly overcast with Garnet Brown, Plate 1. Old foliage: upper side—Dark Cress Green, Plate 31; under side—Light Cress Green, Plate 31.

*Shape.*—Oval pointed.
*Texture.* — Upper side — leathery. Under side—rough. Ribs and veins—ordinary.
*Edge.*—Serrated (saw-toothed).
*Serration.*—Double and single; small.
*Leaf stem.*—Color—Rainette Green, Plate 31. Under side—prickles.
*Stipules.*—Long; bearded.
Wood:
*New wood.*—Color—Biscay Green, Plate 17. Bark—smooth.
*Old wood.*—Color—Jade Green, Plate 31. Bark—smooth.
Thorns:
*Thorns.*—Quantity—on main stalks from base and on laterals from stalk—many. Form—flat base; long; straight and hooked downward. Color when young—Spectrum Red, Plate 1. Position—irregular.
*Prickles and short needles.*—On main stalks and on laterals—none.

I claim:

A new and distinct variety of rose plant of the hybrid tea class, characterized particularly as to novelty by the bright Spectrum Red color of its flowers, lightly overcast with Scarlet Red and suffused with Lemon Chrome at the base of the petals, by the quick repetition of growth, with the top eyes under the flowers breaking into long shoots even before the flowers are in full bloom, and by the long stems of the flowers, substantially as herein shown and described.

HENDRIKUS ANTONIE
MARIA VERSCHUREN.

No references cited.